United States Patent
Sato et al.

(10) Patent No.: US 11,801,205 B2
(45) Date of Patent: Oct. 31, 2023

(54) FILM-FORMING COMPOSITION CONTAINING SURFACTANT OR SURFACTANT AND SALT AS WHITENING AGENT

(71) Applicant: Capsugel Belgium NV, Bornem (BE)

(72) Inventors: Kaori Sato, Kawasaki (JP); Takahisa Takubo, Ayase (JP); Hitomi Doi, Kawasaki (JP)

(73) Assignee: Capsugel Belgium NV, Bornem (BE)

( * ) Notice: Subject to any disclaimer, the term of this patent is extended or adjusted under 35 U.S.C. 154(b) by 119 days.

(21) Appl. No.: 17/253,103

(22) PCT Filed: Jul. 3, 2019

(86) PCT No.: PCT/JP2019/026430
§ 371 (c)(1),
(2) Date: Dec. 16, 2020

(87) PCT Pub. No.: WO2020/009142
PCT Pub. Date: Jan. 9, 2020

(65) Prior Publication Data
US 2021/0275404 A1 Sep. 9, 2021

(30) Foreign Application Priority Data

Jul. 4, 2018 (JP) .................... 2018-127350
Feb. 28, 2019 (JP) .................... 2019-036083

(51) Int. Cl.
| | | |
|---|---|---|
| A61K 8/02 | (2006.01) | |
| A61K 8/11 | (2006.01) | |
| A61K 8/37 | (2006.01) | |
| A61K 8/46 | (2006.01) | |
| A61K 8/65 | (2006.01) | |
| A61K 8/73 | (2006.01) | |
| A61K 8/86 | (2006.01) | |

(52) U.S. Cl.
CPC ............ *A61K 8/0204* (2013.01); *A61K 8/11* (2013.01); *A61K 8/37* (2013.01); *A61K 8/46* (2013.01); *A61K 8/65* (2013.01); *A61K 8/731* (2013.01); *A61K 8/86* (2013.01); *A61K 2800/10* (2013.01); *A61K 2800/26* (2013.01); *A61K 2800/43* (2013.01); *A61K 2800/594* (2013.01); *A61K 2800/92* (2013.01)

(58) Field of Classification Search
CPC .......... A61K 8/0204; A61K 8/11; A61K 8/37; A61K 8/46; A61K 8/65; A61K 8/731; A61K 8/86; A61K 2800/10; A61K 2800/26; A61K 2800/43; A61K 2800/594; A61K 2800/92; A61K 8/39; A61K 8/463; A61K 9/48; A61K 9/4816; A61K 9/4825; A61K 9/70; A61K 47/10; A61K 47/14; A61K 47/26; A61K 47/38; A61K 2800/52; A61K 8/0216; A61K 8/375; A61K 8/64; A61K 8/73; A61K 9/4883; A61K 47/02; A61K 47/12; A61K 47/20; A61K 47/36; A61K 47/42; A61K 47/34; A61Q 1/00; A61Q 19/00
See application file for complete search history.

(56) References Cited

U.S. PATENT DOCUMENTS

| | | |
|---|---|---|
| 2006/0118003 A1 | 6/2006 | Sakata et al. |
| 2009/0010975 A1 | 1/2009 | Shiraishi |
| 2014/0135352 A1 | 5/2014 | Yanagida et al. |

FOREIGN PATENT DOCUMENTS

| | | |
|---|---|---|
| CN | 108576785 | 9/2018 |
| EP | 1574220 | 9/2005 |
| EP | 1754729 | 8/2006 |
| EP | 2179728 | 4/2010 |
| EP | 2338613 | 6/2011 |
| JP | S61280422 | 12/1986 |
| JP | S63280017 | 11/1988 |
| JP | H07124462 | 5/1995 |
| JP | H11147819 | 6/1999 |
| JP | 2002212104 | 7/2002 |
| JP | 2003505565 | 2/2003 |
| JP | 2005538102 | 12/2005 |
| JP | 3759949 | 3/2006 |
| JP | 2008290973 | 12/2008 |
| JP | 2013515715 | 5/2013 |
| WO | WO02/40053 | 5/2002 |
| WO | WO2004/054619 | 7/2004 |
| WO | WO2008/156027 | 12/2008 |
| WO | WO2009/021377 | 2/2009 |

(Continued)

OTHER PUBLICATIONS

International Search Report and Written Opinion for PCT/JP2019/026430, dated Sep. 17, 2019) (w/English translation of International Search Report).
Database WPI, Week 201879, Thomson Scientific, London, GB, AN 2018-79865R, XP002797856 (2017).
International Preliminary Report on Patentability for PCT/EP2020/066201, dated Dec. 23, 2021.

(Continued)

*Primary Examiner* — Robert A Wax
*Assistant Examiner* — Quanglong N Truong
(74) *Attorney, Agent, or Firm* — Klarquist Sparkman, LLP

(57) ABSTRACT

[Problem] Providing a whitened capsule and a whitened film without using any white pigment such as titanium dioxide.
[Solution] Provided is a film, a capsule, and a film forming composition, characterized by comprising: a film-forming polymer; and a whitening agent including either a surfactant or both a surfactant and a salt, and characterized in that the surfactant is selected from a fatty acid ester of polyhydric alcohol, a polyethylene glycol, a polypropylene glycol, a polyalkylene oxide derivative, an alkyl sulfate ester salt, and a saponin.

31 Claims, 3 Drawing Sheets

(56) References Cited

FOREIGN PATENT DOCUMENTS

| | | |
|---|---|---|
| WO | WO2011/080647 | 7/2011 |
| WO | WO2013/006470 | 1/2013 |
| WO | WO2020/009142 | 1/2020 |
| WO | WO2020/249672 | 12/2020 |

OTHER PUBLICATIONS

International Search Report and Written Opinion for PCT/EP2020/066201, dated Nov. 11, 2020.
Notice of Dispatch of Duplicates of a Written Opposition for Japanese Patent No. 6887456, dated Jan. 13, 2022 (w/English translation).
Decision on the Opposition for Japanese Patent No. 6887456, mailed Mar. 3, 2022 (w/English translation).
Office Action for European Application No. 19829882.0, dated Jun. 16, 2021.
International Preliminary Report on Patentability for PCT/JP2019/026430, dated Jan. 7, 2021 (w/English translation of International Search Report).
Third Party Observations filed in EPC Application No. 19829882.0 on Mar. 30, 2022.

FILM-FORMING COMPOSITION CONTAINING SURFACTANT OR SURFACTANT AND SALT AS WHITENING AGENT

CROSS REFERENCE TO RELATED APPLICATIONS

This is the U.S. National Stage of International Application No. PCT/JP2019/026430, filed Jul. 3, 2019, which in turn claims the benefit of Japanese Application No. 2018-127350, filed Jul. 4, 2018 and Japanese Application No. 2019-036083, filed Feb. 28, 2019. The applications are incorporated herein in their entirety.

TECHNICAL FIELD

The present invention relates to a film forming composition used for pharmaceutical preparations and the like purposes and whitened during film formation by a surfactant or by both a surfactant and a salt. The present invention also relates to applications of such a film forming composition to: a capsule and an orodispersible film manufactured using the film forming composition; preparations of a tablet, a granule, and the like drugs coated with the film forming composition; and a film product, a printing ink, and the like products.

In addition, the present invention relates to a light-blocking capsule manufactured of a film forming composition having a higher level of whitening to provide light-blocking effects against various kinds of light including the UV, thereby being capable of keeping the stability of an active ingredient and the quality of the capsule for a prolong period of time, while the light-blocking capsule allows for the quick dissolution of the active ingredient.

BACKGROUND ART

Various colors have been given to various preparations including pharmaceutical products and health food. Some of the purposes of such coloring, among other things, are: making the preparations highly identifiable; providing the preparations with beautiful appearances; and providing light-blocking capability against the light in order for quality maintenance. In particular, in a case of a preparation containing an ingredient that is vulnerable to light, a common practice is adding a light-blocking agent to a capsule film or a coating film so that a light-blocking film of white color can be produced. Furthermore, if necessary, various edible colorants (Blue No. 1, Yellow No. 5, Red No. 3, etc.) or various pigments such as iron sesquioxide, aluminum lakes, or the like substances are added to freely give a desired color to the light-blocking film.

Various whitening agents that give a light-blocking property to the target material have been known. Among such whitening agents, titanium dioxide is one of the most-frequently used. Titanium dioxide is a white pigment characterized by its excellent whiteness, opacity, and coloring ability as well as its extremely high chemical stability. Hence, titanium dioxide has long been used in the field of pharmaceutical products and in the field of cosmetic products.

Some pharmaceutical and cosmetic products have contents that are destabilized by titanium dioxide or whose decomposition is accelerated by the radicals generated from titanium oxide by UV light. Quality maintenance of such products has always been a problem. In addition, Irradiation of light may cause preparations coated with a film containing titanium dioxide to undergo peeling of the film and/or become powdery overtime, making it difficult to keep the preparations in a coated state. As a result, the external appearance of such preparations may be impaired. Another matter of concern is that light, oxygen, and/or moisture may cause decomposition of ingredients contained in the preparations.

Various coating materials for pharmaceutical preparations have been studied thus far. An example of such coating materials is a coating material containing titanium dioxide blended with a radical scavenger (Patent Literature 1: JP11-147819A). Other examples include titanium-dioxide-free coating materials, such as an opaque or translucent hard capsule made of gelatin containing natural calcium powder of average particle size of 3 μm or less (Patent Literature 2: JPH7-124462A) and a coating agent containing talc and/or barium sulfate (Patent Literature 3: JP2002-212104A).

None of the above-mentioned inorganic pigments such as titanium dioxide are soluble in water or in organic solvents, resulting in a more troublesome preparation of the coating liquid. Use of such inorganic pigments has other problems such as: irregular tablet surface and reduced film strength, both caused by the spraying of the suspension; troubles in the coating step of the manufacturing process (e.g., the clogging of spray-nozzle, the dripping of liquid caused by the solid accumulated at the tip end of the nozzle, etc.).

Consideration of the above-mentioned problems has led to studies on titanium-dioxide free light-blocking film compositions such as one containing one or more substances selected from water-soluble calcium salts along with a film base agent of a water-soluble cellulose-based polymer (Patent Literature 4: WO2004/054619A)

PRIOR ART DOCUMENTS

Patent Literature

[Patent Literature 1] JP11-147819A
[Patent Literature 2] JPH7-124482A
[Patent Literature 3] JP2002-212104A
[Patent Literature 4] WO2004/054619A

SUMMARY OF THE INVENTION

Problems to be Solved by the Invention

While various alternative technologies that may replace titanium dioxide as described above have been studied thus far, titanium oxide powder is still widely used as a light-blocking agent in various industrial fields including the food industry and pharmaceutical industry. This is because the very fine particles and the incomparable opacity of titanium dioxide that provide a sufficient blocking ability even with a small dose thereof.

International Agency for Research on Cancer (IARC) changed the classification of the carcinogenicity of titanium dioxide from Group 3 (not classifiable as to its carcinogenicity to humans) to Group 2B (possibly carcinogenic to humans) in June 2006, when it concludes that the results of animal experiment through inhalation and intratracheal injection of pigment grade and ultra fine TiO2 gives sufficient evidence to show the carcinogenicity of TiO2 for animals (Baan R, Staif K, Grosse Y, Secretan B, Ghissassi F, Cogliano V. on behalf of the WHO International Agency for Research on Cancer Monograph Working Group (2006)

Carcinogenicity of carbon black, titanium dioxide, and talc. [cited Jun. 22, 2009], available from: http://oncology.thelancet.com.)

Hence, especially the health food industry has started avoiding capsules containing titanium dioxide, and there has been more and more demand for the development of an alternative light-blocking agent to titanium dioxide. As described earlier, any alternative to the excellent light-blocking agent of titanium dioxide is very hard to find. Currently, there is still no supply of any titanium-dioxide-free light-blocking capsule, the one that is highly demanded by the health food industry.

Solution to Problems

The inventors of the present invention have tried to solve the above-described technical problems to develop an alternative light-blocking method that can replace the use of titanium dioxide, which especially the health food industry has longed for. After several years of screening and experiments, the inventors have discovered that addition of a colorless surfactant or a combination of a colorless surfactant and a colorless salt depending on the kind of the film forming polymer can whiten the film during the formation thereof and provide a beautiful appearance and light-blocking ability that are comparable to the one obtained by the dispersion of titanium dioxide. Also discovered is the fact that the film formed in the above-mentioned way does not fade or change its color even in a hot and humid environment. In a case of using a natural extract saponin as a surfactant, even a saponin having a color such as light brown or the like colors can be used because the whitening is possible for the film in a state of having that color. In addition, according to this whitening technique, the level of whitening and that of the light blocking can be adjusted by changing the amount of the added surfactant and/or that of the added salt. Furthermore, the whitening technique can be combined with the use of other coloring materials, which allows various different colors to be given as desired.

A variety of surfactants are registered as food additives and pharmaceutical additives. Surfactants as food additives are used for the purposes of: emulsification, moistening/dispersion, viscosity control, lubrication, mouthfeel improvement, bacteriostasis, prevention of frozen food denaturation, prevention of chocolate fat bloom, inhibition of starch aging, foaming/defoaming, etc. Surfactants as pharmaceutical additives are widely used as stabilizing agents, lubricants, solubilizers, bases, binders, suspending agents, coating agents, moistening agents, defoaming agents, emulsifiers, fillers, etc.

Likewise, salts (malates, succinates, citrates, phosphates, carbonates, acetates, etc.) are used as food additives, for example, seasonings, pH adjusters, acidulants, acidification preventing agents, thickeners, stabilizers, chelating agents, dispersants, buffering agents, etc. Salts are also used widely as pharmaceutical additives, for example, corrigents, stabilizing agents, buffering agents, binders, suspending agents, isotonizing agents, pH adjusters, foaming agents, disintegrating agents, disintegration aiding agents, soothing agents, solubilizing agents, solubilization aiding agents, etc.

These substances are, most frequently, colorless transparent ingredients. As described earlier, some naturally extracted saponins are colored transparent ingredients having light brown color or the like. Whitening of a film forming polymer during film formation caused by use of a surfactant alone or in combination with a salt is a phenomenon that was discovered by the inventors of the present invention for the first time in history, and it is a really a surprising discovery.

The present invention can provide a film or a capsule having a beautiful white color or a different color with a light blocking property. In particular, for the health food market, a safe-and-secure beautifully-colored light-blocking capsule can be provided by combining with a natural-source colorant such as gardenia.

The technology of the present invention can be used for compositions containing hypromellose (hydroxypropyl methylcellulose), gelatin, and/or pullulan, which are as ordinary raw materials of capsule film. In addition, the technology of the present invention can also be used for coloring products other than capsule films, for example, coloring of band sealing of the capsules, orodispersible film preparations, coating material for tablets and granules, edible film products, inks for food, etc. In addition, the technology of the present invention can be used for a film made by adding the technology of the present invention to a polymer solution having film formability other than those mentioned above and then drying the resultant solution.

The level of whitening can be adjusted by the kind and the amount of use of the surfactant to be used, and by the kind of salt to be used in combination with the surfactant. Hence, the level of whitening can be adjusted from a white color that gives an excellent light-blocking property to a white color that allows the user to see a dimly cloudy image through the film.

The mechanism of whitening has not been revealed yet, but the inventors have found out, through observation using microscopes, that microcrystals were generated in the base agent film during the drying step and that white crystals grew from the microcrystals used as their seeds. Based on the observation, the inventors estimate that the whitening phenomenon be caused by the generation of microcrystals of the surfactant in the base agent film and that the salt assist the generation or the growth of the crystals. An alternative estimation is that the whitening phenomenon be caused by the microcrystals of the surfactant and/or of the salt generated continuously in the base material film during the drying step. Whether a salt is necessary for the occurrence of whitening phenomenon seems to depend on the physical properties or the kind of the film base agent.

Even the use of sodium chloride or potassium chloride can yield the whitening of the film, but the microcrystals of these substances are generated on the film surfaces. Hence, the microcrystals are easily scraped off from the film to deprive the film of the whiteness. In this sense, the whitening caused by the use of sodium chloride or potassium chloride is no match for the present invention where the microcrystals appear in the film and are not easily scraped off from the film, resulting in no color loss and keeping the film in white color.

The polymer base material that can produce the aqueous solution to be used the present invention may be one that is usable for pharmaceutical products and food products as the base material for capsules. Alternatively, a base material that is used for the coating of drugs and food preparations may be used for the same purpose. Cellulose derivatives, gelatins, and pullulan are some of the examples of such an ingredient.

Various types of hypromellose (hydroxypropyl methylcellulose=HPMC) are some of the preferable cellulose derivatives. Specifically, HPMC2910 (containing about 29% of methoxy group and about 10% of hydroxypropoxyl group), HPMC2906 (containing about 29% of methoxy group and about 6% of hydroxypropoxyl group), and HPMC2208 (containing about 22% of methoxy group and about 8% of hydroxypropoxyl group) are some of the preferable HPMCs.

Each of these ingredients may be used alone or in combination with others.

The surfactant used in the present invention is selected from fatty acid esters of polyhydric alcohol, polyethylene glycols, polypropylene glycols, polyalkylene oxide derivatives, alkyl sulfate ester salts, saponins, and the like.

Some examples of the above-mentioned fatty acid esters of polyhydric alcohol are a sucrose fatty acid ester, a sorbitan fatty acid ester, a glycerin fatty acid ester, a polyoxysorbitan fatty acid ester (e.g., a sucrose monolaurate ester, a sucrose palmitate ester, a sorbitan monolaurate ester, and a Polysorbate 80 (a polyoxyethylene sorbitan monooleate). An example of the above-mentioned polyethylene glycols is a polyethylene glycol 4000 (macrogol 4000). Some examples of the above-mentioned polyalkylene oxide derivatives are a polyoxyethylene polyoxypropylene glycol, and a polyoxyethylene alkyl ether, a polyoxyethylene fatty acid ester (e.g., a polyoxyethylene (105) polyoxypropylene (5) glycol, and a polyoxyethylene (160) polyoxypropylene (30) glycol). An example of the alkyl sulfate ester salts is a sodium lauryl sulfate.

The term "saponin" is a generic name for glycosides of steroids or triterpenes (toriterpenoid saponins or steroid saponins). Though widely distributed in the plant kingdom, the triterpenoid saponins are found in not only plants but also in echinoderms such as sea cucumbers and star fish. The saponins to be used as a surfactant in the present invention are any kinds of saponins irrespective of where their raw materials come from, that is, whether the raw material of a particular saponin is animal-derived or plant-derived or which animal/plant it is derived from. Some examples of preferable saponins are quillaja saponin, ginseng saponin, soybean saponin, sophora saponin, tea seed saponin, beet saponin, yucca saponin, and glycyrrhizin.

Each of these surfactants may be used alone or in combination of others. Varying the amount of the surfactant(s) to be added can change the whiteness.

Usually for a total of 100 parts by weight (measured as a dry weight) of a film-forming polymer (e.g., a polymer selected from cellulose derivatives, gelatins, pullulans, etc.), the total amount of the surfactant(s) to be added may range from 0.5 to 30 parts by weight, from 0.7 to 30 parts by weight, or from 1.0 to 30 parts by weight. Preferably, it may range from 0.5 to 15 parts by weight, 0.7 to 15 parts by weight, or from 1.0 to 15 parts by weight. The amount of the surfactant(s) within the above-mentioned ranges may be used for changing the whiteness. Use of surfactant(s) in an amount exceeding 30 parts by weight yields a film that is more brittle and that breaks more easily. Conversely, use of surfactant(s) in an amount less than 0.5 parts by weight may result in no occurrence of any whitening phenomenon, or may result in the occurrence of a whitening phenomenon with a very light color, which makes the light blocking effect less expected.

The salts to be used in the present invention are sodium salts and/or potassium salts and/or ammonium salts. Specifically, sodium malate, sodium succinate, sodium citrate, sodium polyphosphate, sodium bicarbonate (baking soda), potassium acetate, potassium carbonate, dipotassium hydrogenphosphate, potassium dihydrogenphosphate, disodium hydrogenphosphate, sodium dihydrogenphosphate, sodium pyrophosphate dehydrate, and ammonium chloride are some examples of the salts to be used in the present invention.

Each of these salts may be used alone or in combination with others. Varying the amount of the salt(s) to be added can change the whiteness.

Usually for a total of 100 parts by weight (measured as a dry weight) of film-forming polymer (e.g., a polymer selected from cellulose derivatives, gelatins, pullulans, etc.), a total amount of salt(s) in the range of 0.5 to 30 parts by weight can change the whiteness.

In a case where a hard capsule is manufactured using the film forming composition of the present invention, dipping solution (capsule dipping solution) is prepared using a gelling agent, some examples of which include carrageenan, gellan gum, agar, pectin, gelatin, xanthan gum, locust bean gum, curdlan, alginic acid, sodium alginate, guar gum, arabian gum, glucomannan, tamarind seed gum, furcelleran, tara gum, and karaya gum. However, these are not the only possible gelling agents usable in this case. In addition to the additives mentioned thus far, some other substances may be added when necessary. Some examples of such other substances include gelling aiding agents, plasticizers, pH adjusters, sweeteners, acidulants, preservatives, and flavoring agents. The gelling agents may be used in an amount ranging from 0 to 10%, and preferably from 0 to 5%.

Some examples of the plasticizers include triethyl citrate, glycerin, propylene glycol, D-mannitol, D-sorbitol, trehalose, polyethylene glycol, triacetin, and phthalate esters. Some examples of the pH adjusters include phosphoric acid, hydrochloric acid, citric acid, glycine, gluconic acid, succinic acid, acetic acid, tartaric acid, lactic acid, fumaric acid, boric acid, maleic acid, sulfuric acid, malic acid, ammonia, hydroxides, amines, and salts thereof.

The film forming composition of the present invention may contain a colorant other than the white one. For instance, colorants of black or chromatic colors may be blended in the film forming composition of the present invention. The above-mentioned chromatic colors are all the colors except black, white, and gray colors.

In a case of using colorants for coating purposes in pharmaceutical preparations or in health food preparations, the colorants of any chromatic colors may be used as long as such colorants are allowed to be used in the field of pharmaceutics and food. Some examples of such colorants include tar colorant lakes, water-soluble tar colorants, and natural colorants.

Some specific examples of tar colorant lakes include Food Blue No. 1 aluminum lake, Food Blue No. 2 aluminum lake, Food Red No. 2 aluminum lake, Food Red No. 3 aluminum lake, Food Red No. 40 aluminum lake, Food Yellow No. 4 aluminum lake, Food Yellow No. 5 aluminum lake, and Food Green No. 3 aluminum lake. Some specific examples of water-soluble tar colorants include Food Blue No. 1, Food Blue No. 2, Food Yellow No. 4, Food Yellow No. 5, Food Red No. 2, Food Red No. 3, Food Red No. 40, Food Red No. 102, Food Red No. 104, Food Red No. 105, Food Red No. 106, and Food Green No. 3. Some specific examples of natural colorants include caramel colorant, gardenia colorant, safflower colorant, turmeric colorant, monuscus colorant, carotene, beet red, tomato colorant, cochineal colorant, lac colorant, perilla colorant, red cabbage colorant, red radish colorant, red rice colorant, adzuki bean colorant, purple sweet potato colorant, purple yam colorant, purple corn colorant, grape pericarp colorant, colorants of various berries, grape juice colorant, *Haematococcus pluvialis* colorant, red pepper colorant, Annatto colorant, *Spirulina* colorant, cacao colorant, persimmon colorant, kaollang colorant, onion colorant, tamarind colorant, green tea powder, squid ink, Phaffia colorant, pecan nut colorant, rutin, logwood colorant, saffron colorant, *Lonicera graciipes* colorant, colorants of various teas, laver colorant, hibiscus colorant, paprika powder, plum colorant, cherry colorant, chicory colorant, juice, vegetable juice, red currant colorant, marigold colorant, chlorella powder, sodium norbixin, sodium iron chlorophyllin, sodium copper chlorophyllin, copper chlorophyll, naked-barley green-leaf extract powder, naked-barley green-leaf aojiru dry powder, and naked-barley green-leaf extract. Some specific examples of other chromatic color colorants include methylrosanilinnium chloride, carmine, Photosensilizer 201, Permanent violet-R-special, methylene blue, riboflavin tetrabutyrate, riboflavin, riboflavin sodium phosphate, iron sesquioxide, yellow iron sesquioxide, and black iron oxide. Pearl pigments made from fine powder of fish scale guanine, nacreous layer of shellfish, mica, silicon dioxide, etc. or the like pigments may be used in an appropriate amount for the purpose of giving nacreous luster.

Some specific examples of plasticizers to be used for the film forming composition of the present invention include triethyl citrate, glycerin, sesame oil, D-sorbitol/sorbitan liquid, vegetable oils, medium-chain fatty-acid triglyceride, triacetin, castor oil, dioctyl phthalate, phytosterol, propylene glycol, polysorbate, and macrogol. Some specific examples of sweeteners include aspartame, acesulfame potassium, sweet hydrangea leaf powder, liquid sugar, fructose, glucose, reduced maltose syrup, liquorice, xylitol, glycine, glycerin, glycyrrhizinate, brown sugar, saccharin, sucralose, stevia extract, purified sucrose, purified honey, D-sorbitol, maltitol, maltose, and D-mannitol.

In addition, some specific examples of acidulants include adipic acid, itaconic acid, citric acid, trisodium citrate, glucono delta lactone, gluconic acid, potassium gluconate, sodium gluconate, succinic acid, monosodium succinate, disodium succinate, sodium acetate, tartaric acid, lactic acid, sodium lactate, acetic acid, phytic acid, fumaric acid, malic acid, and phosphoric acid. Some specific examples of preservatives include benzoic acid, sodium benzoate, paraoxybenzoate esters, sodium sulfite, sodium hyposulfite, sodium pyrosulfite, potassium pyrosulfite, propionic acid, calcium propionate, sodium propionate, *Styrax japonica* extract, *Artemisia capillaris* extract, milt protein extract, sorbic acid compounds, sodium dehydroacetate, nisin, sulfur dioxide, pectin degradation product, and ε-polylysine.

In addition, some specific examples of flavoring agents include essences of various kinds, flavors, pepper mint, menthol, Japanese mint, cinnamon, fennel, and camphor.

The hard capsule according to the present invention may be manufactured by a method of manufacturing ordinary capsules. By way of example, a case of manufacturing a gelatin capsule will be described below. To begin with, a gelatin from 20 to 40 parts by weight is dissolved evenly into hot water to prepare a transparent dipping solution of light yellow color, which is derived from the color of the gelatin. The surfactant(s) (and the salt(s)) of the present invention serving as the whitening agent(s) are added to the dipping solution at this stage. After adjusting the viscosity of the resultant dipping solution, a stainless-steel molding pin is dipped in the dipping solution. The pin is lifted out of the dipping solution and the dipping solution on the lifted-out pin is immediately cooled to allow it to become a gel having a certain thickness that is appropriate for a capsule. Then, the gel thus obtained is dried and unnecessary portions thereof are cut off to produce a body and a cap. Then, a capsule is manufactured of a pair of a body and a cap by fitting them together.

It is preferable to select the most appropriate surfactant(s) or the most appropriate combination of the surfactant(s) and the salt(s) In accordance with the kind of polymer that can be dissolved to form the aqueous solution. Some examples of the combinations that yield particularly higher whitening level and particularly excellent light-blocking ability for cases of HPMCs include combinations of: a polyoxyethylene (105) polyoxypropylene (5) glycol and a sodium malate; a polyoxyethylene (105) polyoxypropylene (5) glycol and a sodium citrate; a polyoxyethylene (105) polyoxypropylene (5) glycol and a sodium succinate; a polyoxyethylene (105) polyoxypropylene (5) glycol and a sodium bicarbonate (baking soda); a sucrose monolaurate ester and sodium malate; a sucrose monolaurate ester and a potassium carbonate; a sucrose monolaurate ester and a dipotassium hydrogenphosphate; a sucrose monolaurate ester and a potassium dihydrogenphosphate; a sucrose monolaurate ester and a disodium hydrogenphosphate; a sucrose monolaurate ester and a sodium dihydrogenphosphate; a sucrose monolaurate ester and a sodium bicarbonate (baking soda); a sucrose monolaurate ester and a sodium citrate; a sucrose monolaurate ester and a sodium succinate; a polyoxyethylene (160) polyoxypropylene (30) glycol and a sodium malate; a polyoxyethylene (160) polyoxypropylene (30) glycol and a sodium succinate; a polyoxyethylene (160) polyoxypropylene (30) glycol and a sodium citrate; a sucrose palmitate ester and a sodium malate; a sucrose palmitate ester and a sodium succinate; a macrogol 4000 and a sodium malate; a Polysorbate 80 and a sodium malate; and a quillaja saponin and a sodium succinate. Some examples of such combinations for cases of gelatins include combinations of: a sucrose monolaurate ester and a sodium polyphosphate; a sucrose monolaurate ester and a disodium hydrogenphosphate; a sucrose monolaurate ester and a sodium pyrophosphate dehydrate; a polyoxyethylene (105) polyoxypropylene (5) glycol and a sodium polyphosphate; a quillaja saponin and a sodium polyphosphate; and a quillaja saponin and a sodium pyrophosphate dehydrate. Some examples for cases of pullulans include: use of a polyoxyethylene (105) polyoxypropylene (5) glycol alone, and a combination of a polyoxyethylene (105) polyoxypropylene (5) glycol and a sodium bicarbonate (baking soda) and the like combinations.

Of those mentioned above, particularly preferably combinations for the cases of HPMCs include combinations of: a polyoxyethylene (105) polyoxypropylene (5) glycol and a sodium malate; a polyoxyethylene (105) polyoxypropylene (5) glycol and a sodium citrate; a sucrose monolaurate ester and a sodium malate; a sucrose monolaurate ester and a sodium citrate; a sucrose monolaurate ester and a dipotassium hydrogenphosphate; a sucrose monolaurate ester and a disodium hydrogenphosphate; a sucrose monolaurate ester and a sodium dihydrogenphosphate; a sucrose monolaurate ester and a potassium carbonate; a sucrose monolaurate ester and a potassium dihydrogenphosphate; a sucrose monolaurate ester and a sodium bicarbonate (baking soda); a sucrose monolaurate ester and a sodium succinate; a polyoxyethylene (160) polyoxypropylene (30) glycol and a sodium malate; a polyoxyethylene (160) polyoxypropylene (30) glycol and a sodium succinate; a polyoxyethylene (160) polyoxypropylene (30) glycol and a sodium citrate; a sucrose palmitate ester and a sodium malate; a sucrose palmitate ester and a sodium succinate; a macrogol 4000 and a sodium malate; a Polysorbate 80 and a sodium malate; and a quillaja saponin and a sodium succinate. Particularly preferable combinations for the cases of gelatins include combinations of: a sucrose monolaurate ester and a sodium polyphosphate; a sucrose monolaurate ester and a disodium hydrogenphosphate; a sucrose monolaurate ester and a sodium pyrophosphate dehydrate; a polyoxyethylene (105) polyoxypropylene (5) glycol and a sodium polyphosphate; a quillaja saponin and a sodium polyphosphate; and a quillaja saponin and a sodium pyrophosphate dehydrate. For the cases of pullulans; use of a polyoxyethylene (105) polyoxypropylene (5) glycol alone is particularly preferable.

Formation of the film is carried out by: firstly dissolving a particular film base agent in hot or cold water that is appropriate for the dissolution of the particular film base agent: then adding the selected surfactant(s) and, if necessary, the selected salt(s) into the solution, optionally adding necessary additives in accordance with the specific purposes, and thereby obtaining a target aqueous solution; and then carrying out the drying of the solution by heating or by natural drying. Temperature conditions at the time of drying may affect the level of whitening. Hence, it is desirable to select the drying conditions that are appropriate for the particular combination of the base material, the surfactant (s), and the salt(s).

Some examples of drying conditions include: high-temperature drying in an oven at a temperature of 60° C. for 15 minutes, and natural drying at room temperature.

Advantageous Effects of the Invention

The present invention provides a technique of whitening a film without using titanium oxide, whose possible carcinogenicity is concerned. Instead, the technique uses ingredients that are harmless to humans, specifically, the surfactant(s), or a combination of the surfactant(s) and the salt(s), that has been used thus far in the fields of pharmaceutical products and food products. The level of the whitening is adjustable, from a level where the whitened film still allows a dim image to be seen though the film to a level where the whitening has a light-blocking effect that is comparable to the one obtained by use of titanium dioxide. Hence, the technique can be preferably used both for general coloring purposes and for preparations of pharmaceutical products and food products that are unstable to light.

In addition, the film manufactured by use of the film forming composition of the present invention does not suffer from the removal of its white color, which would otherwise be caused by rubbing the film. The film manufactured by use of the film forming composition of the present invention has an excellent solubility, is capable of forming a white-colored film that is stable for a prolonged period of time. In addition, if used together with a colorant of a different color, the film forming composition of the present invention can provide a colored opaque film.

Hence, the film forming composition of the present invention can provide, especially to the health food market, a safe-and-secure beautifully-colored light-blocking capsule and film if combined with a natural-source colorant such as gardenia.

TESTING EXAMPLES

Figure 1A:
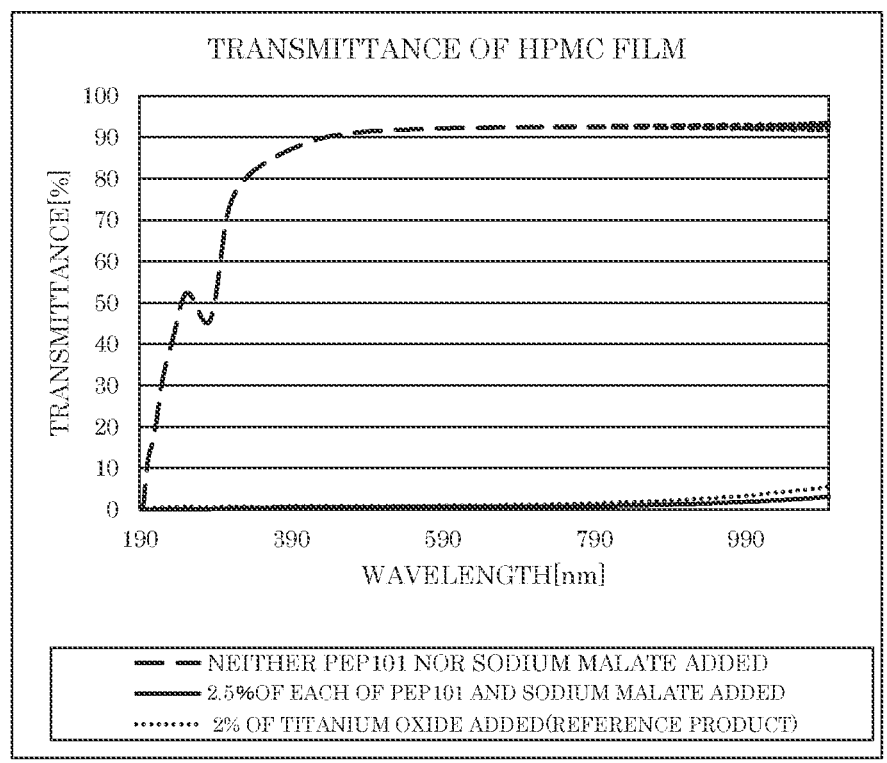
FIG. 1A shows: the light-blocking effect of a white-colored film manufactured by use of a whitening agent containing 2.5 parts by weight of sodium malate and 2.5 parts by weight of polyoxyethylene (105) polyoxypropylene (5) glycol along with 100 parts by weight of hydroxypropyl methylcellulose; and the light-blocking effect of a film manufactured without using the whitening agent.

Whitening during the film formation was tested by preparing test samples containing various kinds of film-forming polymers and surfactants alone or both surfactants and salts.

In the tables, the figures for the individual salts and surfactants are their respective amounts in part by weight expressed with the weight (dry weight) of the film base material being 100 parts by weight.

The white-color proportion and the white-color depth were determined through visual observation by use of the following criteria. Note that the term "white-color proportion" Is the proportion of the whitened area irrespective of the "white-color depth." The term "white-color depth" indicates the depth of the white color of each portion that looks white.

White-color proportion: $\alpha$=100 to 90%, $\beta$=90 to 80%, $\gamma$=80 to 70%, $\delta$=70% or lower, $\varepsilon$=0%

White-color depth: $\alpha$=purely white, $\beta$=white, $\gamma$=translucent, $\delta$=dimly white, $\varepsilon$=transparent The stabilities of the films were assessed by observing the level of whiteness after 6-week storage under an environment of a temperature of 40° C. and a relative humidity of 75%.

The films were manufactured by the following Methods A, B, and C.

A: An ordinary temperature gel was poured onto a glass plate that has been heated in an oven at 105° C. (immediately after the glass plate was taken out of the oven at 105° C.). The gel, together with the glass plate, was immediately dried in an oven at 60° C. for 15 minutes.

B: An ordinary temperature gel was poured onto a glass plate that has been heated in an oven at 105° C. (note that the gel was poured onto the glass plate at the timing when the glass plate was cooled down to about 70° C. (the temperature was measured by use of a radiation thermometer)). The gel and the glass plate were immediately dried in an oven at 60° C. for 15 minutes.

C: The gel was naturally dried in a room.

TABLE 1

Examples using HPMC2910 and PEP101

| Formulation | 1-1 | 1-2 | 1-3 | 1-4 | 1-5 | 1-6 | 1-7 | 1-8 | 1-9 | 1-10 | 1-11 |
|---|---|---|---|---|---|---|---|---|---|---|---|
| HPMC2910 | 100 | 100 | 100 | 100 | 100 | 100 | 100 | 100 | 100 | 100 | 100 |
| Na malate | 2.5 | | | | | | 3.75 | 1.25 | 10 | 10 | 1.25 |
| 2Na succinate | | 2.5 | | | | | | | | | |
| 3Na citrate | | | 2.5 | | | | | | | | |
| Na polyphosphate | | | | 2.5 | | | | | | | |
| Na bicarbonate | | | | | 2.5 | | | | | | |
| PEP101 | 2.5 | 2.5 | 2.5 | 2.5 | 2.5 | 2.5 | 1.25 | 3.75 | 10 | 10 | 1.25 |
| Additive amount | 5 | 5 | 5 | 5 | 5 | 2.5 | 5 | 5 | 20 | 20 | 2.5 |
| White-color proportion | α | α | α | α | β | δ | α | β | α | α | α |
| White-color depth | α | β | α | γ | β | γ | α | β | α | γ | β |
| Stability | No change | No change | No change | No change | White color deepened | — | No change | No change | No change | — | — |
| Manufacturing method | A | A | A | A | A | A | A | A | A | C | A |

The HPMC that was used in the test of this table is a product of Shin-Etsu Chemical Co., Ltd.

Table 1 shows the results of testing by use of HPMC2910 as the film base material and polyoxyethylene (105) polyoxypropylene (5) glycol (PEP101) as the surfactant.

Even when the polyoxyethylene (105) polyoxypropylene (5) glycol was used alone, a certain whitening effect was observed, but a greater whitening effect was more likely to be obtained in the presence of the salt. In addition, the film manufactured by Method A had deeper white color than the corresponding film manufactured by Method C.

TABLE 2

Examples using HPMC2910 and sucrose monolaurate ester

| Formulation | 2-1 | 2-2 | 2-3 | 2-4 | 2-5 | 2-6 | 2-7 | 2-8 | 2-9 |
|---|---|---|---|---|---|---|---|---|---|
| HPMC2910 | 100 | 100 | 100 | 100 | 100 | 100 | 100 | 100 | 100 |
| Na malate | 2.5 | 1.25 | 1.25 | 3.75 | 10 | | 10 | | |
| 2Na succinate | | | | | | | | 2.5 | 1.25 |
| 3Na citrate | | | | | | | | | |
| Na polyphosphate | | | | | | | | | |
| Na bicarbonate | | | | | | | | | |
| K acetate | | | | | | | | | |
| K carbonate | | | | | | | | | |
| 2K hydrogenphosphate | | | | | | | | | |
| K dihydrogenphosphate | | | | | | | | | |
| Ammonium chloride | | | | | | | | | |
| Sucrose monolaurate ester | 2.5 | 1.25 | 3.75 | 1.25 | 10 | 2.5 | 10 | 2.5 | 1.25 |
| Additive amount | 5 | 2.5 | 5 | 5 | 20 | 2.5 | 20 | 5 | 2.5 |
| White-color proportion | α | β | α | α | α | ε | δ | α | δ |
| White-color depth | α | β | α | β | α | ε | β | α | δ |
| Stability | No change | No change | No change | No change | No change | — | — | No change | Whitening a little further |
| Manufacturing method | A | A | A | A | A | A | C | A | A |

Examples using HPMC2910 and sucrose monolaurate ester

| Formulation | 2-10 | 2-11 | 2-12 | 2-13 | 2-14 | 2-15 | 2-16 | 2-17 | 2-18 |
|---|---|---|---|---|---|---|---|---|---|
| HPMC2910 | 100 | 100 | 100 | 100 | 100 | 100 | 100 | 100 | 100 |
| Na malate | | | | | | | | | |
| 2Na succinate | | | | | | | | | |
| 3Na citrate | 2.5 | 1.25 | | | | | | | |
| Na polyphosphate | | | 2.5 | | | | | | |
| Na bicarbonate | | | | | | | | 2.5 | |
| K acetate | | | | | 2.5 | | | | |
| K carbonate | | | | | | 2.5 | | | |
| 2K hydrogenphosphate | | | | | | | 2.5 | | |
| K dihydrogenphosphate | | | | | | | | 2.5 | |
| Ammonium chloride | | | | | | | | | 2.5 |
| Sucrose monolaurate ester | 2.5 | 1.25 | 2.5 | 2.5 | 2.5 | 2.5 | 2.5 | 2.5 | 2.5 |
| Additive amount | 5 | 2.5 | 5 | 5 | 5 | 5 | 5 | 5 | 5 |
| White-color proportion | β | α | α | δ | α | α | α | α | δ |
| White-color depth | β | β | γ | α | α | α | α | α | β |

TABLE 2-continued

| Stability | No change | No change | No change | — | — | — | — | — | — |
|---|---|---|---|---|---|---|---|---|---|
| Manufacturing method | A | A | A | A | A | A | A | A | A |

Table 2 shows the results of testing by use of HPMC2910 as the film base material and sucrose monolaurate ester as the surfactant.

The use of sucrose monolaurate ester alone did not cause whitening to occur. A greater whitening effect was obtained in the presence of the salt. In addition, the film manufactured by Method A had a broader white-colored area and a deeper white color than the corresponding film manufactured by Method C.

TABLE 3

| Formulation | 3-1 | 3-2 | 3-3 | 3-4 | 3-5 |
|---|---|---|---|---|---|
| HPMC2910 | 100 | 100 | 100 | 100 | 100 |
| Na malate |  | 5 |  |  |  |
| 3Na citrate | 2.5 |  |  |  |  |
| 2Na hydrogenphosphate |  |  | 2.5 |  |  |
| 2Na succinate |  |  |  | 2.5 |  |
| Na bicarbonate |  |  |  |  | 2.5 |
| Quillaja saponin | 2.5 | 2.5 | 2.5 | 2.5 | 2.5 |
| Additive amount | 5 | 7.5 | 5 | 5 | 5 |
| White-color proportion | δ | γ | δ | α | γ |
| White-color depth | δ | β | γ | α | β |
| Manufacturing method | A | A | A | A | A |

Table 3 shows the results of testing by use of HPMC2910 as the film base material and quillaja saponin as the surfactant.

Quillaja saponin is a natural extract and its solution is a transparent solution having a light brown color or the like colors. Use of quillaja saponin gives a light brownish white color. The use of 2.5 parts by weight of quillaja saponin and 2.5 parts by weight of disodium succinate rendered the film having both an excellent white-color proportion and an excellent white-color depth.

TABLE 4

Examples using either HPMC2208 or Mixed HPMC (HPMC2906 + HPMC2910) together with either Sucrose monolaurate ester or PEP-101

| Formulation | 4-1 | 4-2 | 4-3 | 4-4 | 4-5 | 4-6 | 4-7 | 4-8 |
|---|---|---|---|---|---|---|---|---|
| Mixed HPMC (HPMC2906 + HPMC2910) |  |  |  |  | 100 | 100 | 100 | 100 |
| HPMC2208 | 100 | 100 | 100 | 100 |  |  |  |  |
| Na malate | 2.5 | 2.5 | 2.5 | 2.5 | 2.5 | 2.5 |  |  |
| 2Na succinate |  |  |  |  |  |  | 2.5 |  |
| 3Na citrate |  |  |  |  |  |  |  | 2.5 |
| Na polyphosphate |  |  |  |  |  |  |  |  |
| Na bicarbonate |  |  |  |  |  |  |  |  |
| K carbonate |  |  |  |  |  |  |  |  |
| 2K hydrogenphosphate |  |  |  |  |  |  |  |  |
| K dihydrogenphosphate |  |  |  |  |  |  |  |  |
| 2Na hydrogenphosphate |  |  |  |  |  |  |  |  |
| Na dihydrogenphosphate |  |  |  |  |  |  |  |  |
| Sucrose monolaurate ester |  | 2.5 |  | 2.5 |  | 2.5 | 2.5 | 2.5 |
| PEP-101 | 2.5 |  | 2.5 |  | 2.5 |  |  |  |
| Additive amount | 5 | 5 | 5 | 5 | 5 | 5 | 5 | 5 |
| White-color proportion | δ | α | δ | δ | δ | α | δ | α |
| White-color depth | δ | α | δ | δ | δ | α | δ | α |
| Stability | No change | No change | — | — | — | — | No change | No change |
| Manufacturing method | A | A | C | C | A | A | A | A |

Examples using either HPMC2208 or Mixed HPMC (HPMC2906 + HPMC2910) together with either Sucrose monolaurate ester or PEP-101

| Formulation | 4-9 | 4-10 | 4-11 | 4-12 | 4-13 | 4-14 | 4-15 | 4-16 |
|---|---|---|---|---|---|---|---|---|
| Mixed HPMC (HPMC2906 + HPMC2910) | 100 | 100 | 100 | 100 | 100 | 100 | 100 | 100 |
| HPMC2208 |  |  |  |  |  |  |  |  |
| Na malate |  | 2.5 |  |  |  |  |  |  |
| 2Na succinate |  |  |  |  |  |  |  |  |
| 3Na citrate |  |  |  |  |  |  |  |  |
| Na polyphosphate | 2.5 |  |  |  |  |  |  |  |
| Na bicarbonate |  |  | 2.5 |  |  |  |  |  |
| K carbonate |  |  |  | 2.5 |  |  |  |  |
| 2K hydrogenphosphate |  |  |  |  | 2.5 |  |  |  |
| K dihydrogenphosphate |  |  |  |  |  | 2.5 |  |  |
| 2Na hydrogenphosphate |  |  |  |  |  |  | 2.5 |  |
| Na dihydrogenphosphate |  |  |  |  |  |  |  | 2.5 |

TABLE 4-continued

| | | | | | | | | |
|---|---|---|---|---|---|---|---|---|
| Sucrose monolaurate ester PEP-101 | 2.5 | 2.5 | 2.5 | 2.5 | 2.5 | 2.5 | 2.5 | 2.5 |
| Additive amount | 5 | 5 | 5 | 5 | 5 | 5 | 5 | 5 |
| White-color proportion | δ | γ | α | α | α | α | α | α |
| White-color depth | δ | γ | α | α | α | α | α | α |
| Stability | No change | — | — | — | — | — | — | — |
| Manufacturing method | A | C | A | A | A | A | A | A |

Table 4 shows the results of testing by use of either HPMC2208 or a mixture of HPMC2910 and HPMC2906 as the film base material together with either sucrose monolaurate ester or polyoxyethylene (105) polyoxypropylene (5) glycol (PEP2.5) as the surfactant and the respective salts.

For both of the base materials, the films formed by Method A rendered broader white-color areas and deeper white colors than their corresponding films formed by Method C.

TABLE 5

Examples using HPMC2910 and various whitening agents as well as Method A of drying

| Formulation | 5-1 | 5-2 | 5-3 | 5-4 | 5-5 | 5-6 | 5-7 | 5-8 | 5-9 | 5-10 |
|---|---|---|---|---|---|---|---|---|---|---|
| HPMC2910 | 100 | 100 | 100 | 100 | 100 | 100 | 100 | 100 | 100 | 100 |
| Na malate | 2.5 | | | | 2.5 | | 2.5 | | | 2.5 |
| 2Na succinate | | 2.5 | | | | 2.5 | | | | |
| 3Na citrate | | | 2.5 | | | | | | | |
| Na polyphosphate | | | | 2.5 | | | | | | |
| Sucrose palmitate ester | | | | | 2.5 | 2.5 | | 2.5 | | |
| Polysorbate 80 | | | | | | | | | | 2.5 |
| PLONON 188P | 2.5 | 2.5 | 2.5 | 2.5 | | | | | | |
| Macrogol 4000 | | | | | | | | 2.5 | 2.5 | |
| Additive amount | 5 | 5 | 5 | 5 | 5 | 5 | 5 | 2.5 | 2.5 | 5 |
| White-color proportion | α | α | α | γ | α | α | α | ε | ε | α |
| White-color depth | α | α | α | β | α | α | α | ε | ε | α |
| Manufacturing method | A | A | A | A | A | A | A | A | A | A |

Table 5 shows the results of testing by use of HPMC2910 as the film base material together with respective ones selected from sucrose palmitate ester, polyoxyethylene sorbitan monooleate (Polysorbate 80), polyoxyethylene (180) polyoxypropylene (30) glycol (PLONON 188P), and polyethylene glycol 4000 (macrogol 4000) as respective surfactants.

TABLE 6

Examples using HPMC2910 and either sucrose monolaurate ester or PEP101 as well as Method B of drying

| Formulation | 6-1 | 6-2 | 6-3 | 6-4 | 6-5 | 6-6 | 6-7 | 6-8 | 6-9 | 6-10 |
|---|---|---|---|---|---|---|---|---|---|---|
| HPMC2910 | 100 | 100 | 100 | 100 | 100 | 100 | 100 | 100 | 100 | 100 |
| Na malate | 2.5 | 1.25 | 2.5 | 1.25 | 1.25 | 0.625 | 1.25 | 0.625 | 0 | 0 |
| Sucrose monolaurate ester | 2.5 | 3.75 | | | 1.25 | 1.875 | | | 1 25 | |
| PEP101 | | | 2.5 | 3.75 | | | 1.25 | 1.875 | | 1.25 |
| Additive amount | 5 | 5 | 5 | 5 | 2.5 | 2.5 | 2.5 | 2.5 | 1.25 | 1.25 |
| White-color proportion | β | γ | β | δ | δ | δ | δ | δ | ε | ε |
| White-color depth | α | β | α | δ | γ | δ | δ | δ | ε | ε |
| Manufacturing method | B | B | B | B | B | B | B | B | B | B |

Table 6 shows the results of testing by use of HPMC2910 as the film base material and either sucrose monolaurate ester or polyoxyethylene (105) polyoxypropylene (5) glycol (PEP101) as the surfactant together with Method B of film formation. When the films formed by Method B with their corresponding ones formed by Method A (see Tables 1 and 2), Method A tended to render films with higher levels of whitening than Method B.

TABLE 7

Examples using HPMC2910 and either sodium lauryl sulfate or sorbitan monolaurate ester

| Formulation | 7-1 | 7-2 | 7-3 | 7-4 |
|---|---|---|---|---|
| HPMC2910 | 100 | | | 100 |
| Mixed HPMC (HPMC2906 + HPMC2910) | | 100 | | |
| HPMC2208 | | | 100 | |
| Na malate | 2.5 | 2.5 | 2.5 | 1.25 |
| Sodium lauryl sulfate | | | | 1.25 |
| Sorbitan monolaurate ester | 2.5 | 2.5 | 2.5 | |
| Additive amount | 5 | 5 | 5 | 2.5 |
| White-color proportion | δ | δ | δ | δ |
| White-color depth | δ | δ | δ | δ |
| Stability | No change | No change | No change | No change |
| Manufacturing method | A | A | A | A |

Table 7 shows the results or testing by use or various HPMCs as the film base material and alkyl sulfate ester salt (either sodium lauryl sulfate or sorbitan monolaurate ester) as the surfactant together with Method A of film formation.

TABLE 8

Examples using either HPMC2208 or mixed HPMC (HPMC2910 + HPMC2208) and sucrose monolaurate ester as well as Method B of drying

| Formulation | 8-1 | 8-2 | 8-3 | 8-4 | 8-5 | 8-6 | 8-7 | 8-8 | 8-9 |
|---|---|---|---|---|---|---|---|---|---|
| Mixed HPMC (HPMC2910 + HPMC2208) | 100 | 100 | 100 | 100 | | | | | 100 |
| HPMC2208 | | | | | 100 | 100 | 100 | 100 | |
| Na malate | 0 | 1.25 | 2.5 | 3.75 | 0 | 1.25 | 2.5 | 3.75 | 5 |
| Sucrose monolaurate ester | 0 | 3.75 | 2.5 | 1.25 | 0 | 3.75 | 2.5 | 1.25 | 1.25 |
| Additive amount | 0 | 5 | 5 | 5 | 0 | 5 | 5 | 5 | 6.25 |
| White-color proportion | ε | δ | β | γ | ε | δ | δ | γ | α |
| White-color depth | ε | δ | β | α | ε | δ | δ | α | α |
| Manufacturing method | B | B | B | B | B | B | B | B | B |

Table 8 shows the results of testing by use of either HPMC2208 alone or a mixture of HPMC2910 and HPMC2208 as the film base material and sucrose monolaurate ester as the surfactant together with Method B of film formation. Use of the mixture of HPMC2910 and HPMC2208, 5 parts by weight of sodium malate, and 1.25 parts by weight of sucrose monolaurate ester rendered a film having both an excellent white-color proportion and an excellent white-color depth.

TABLE 9

Examples of using pullulan

| Formulation | 9-1 | 9-2 | 9-3 | 9-4 | 9-5 | 9-6 | 9-7 | 9-8 |
|---|---|---|---|---|---|---|---|---|
| Pullulan | 100 | 100 | 100 | 100 | 100 | 100 | 100 | 100 |
| Na malate | 2.5 | | | | | 2.5 | | |
| 2Na succinate | | 2.5 | | | | | 2.5 | |
| 3Na citrate | | | 2.5 | | | | | 2.5 |
| Na polyphosphate | | | | 2.5 | | | | |
| Na bicarbonate | | | | | 2.5 | | | |
| Pyrophosphate dehydrate | | | | | | | | |
| Sucrose monolaurate ester | | | | | | 2.5 | 2.5 | 2.5 |
| PEP101 | 2.5 | 2.5 | 2.5 | 2.5 | 2.5 | | | |
| Additive amount | 5 | 5 | 5 | 5 | 5 | 5 | 5 | 5 |
| White-color proportion | γ | γ | γ | γ | β | δ | δ | δ |
| White-color depth | γ | γ | γ | γ | β | δ | δ | δ |
| Manufacturing method | C | C | C | C | C | C | C | C |

Examples of using pullulan

| Formulation | 9-9 | 9-10 | 9-11 | 9-12 | 9-13 | 9-14 | 9-15 | 9-16 |
|---|---|---|---|---|---|---|---|---|
| Pullulan | 100 | 100 | 100 | 100 | 100 | 100 | 100 | 100 |
| Na malate | | | | | 2.5 | | | |
| 2Na succinate | | | | | | | | |
| 3Na citrate | | | | | | | | |
| Na polyphosphate | 2.5 | | | | | 5 | | |
| Na bicarbonate | | 2.5 | | | | | | |
| Pyrophosphate dehydrate | | | | | | | | 5 |
| Sucrose monolaurate ester | 2.5 | 2.5 | | 2.5 | | 5 | 5 | 5 |
| PEP101 | | | 2.5 | | | | | |

TABLE 9-continued

| Additive amount | 5 | 5 | 2.5 | 2.5 | 2.5 | 10 | 10 | 10 |
|---|---|---|---|---|---|---|---|---|
| White-color proportion | δ | δ | α | δ | ε | β | β | β |
| White-color depth | δ | δ | β | δ | ε | δ | δ | δ |
| Manufacturing method | C | C | C | C | C | C | C | C |

Table 9 shows the results of testing by use of pullulan as the film base material and either polyoxyethylene (105) polyoxypropylene (5) glycol (PEP101) or sucrose monolaurate ester as the surfactant. In the cases of this base agent, use of polyoxyethylene (105) polyoxypropylene (5) glycol (PEP101) alone with no salt at all allowed the whitening phenomenon to occur. Use of salts even tended to lower, rather than enhance, the level of whitening. It was discovered that the use of sucrose monolaurate ester rendered dimly whitening irrespective of whether to use the sucrose monolaurate ester alone or in combination of any salt.

of this base agent, it was observed that use of either polyoxyethylene (105) polyoxypropylene (5) glycol (PEP101) or sucrose monolaurate ester alone with no salt at al allowed the whitening phenomenon to occur (see Formulations 92 and 93). Use of any of sucrose monolaurate ester and polyoxyethylene (105) polyoxypropylene (5) glycol (PEP101) in combination with any of sodium polyphosphate, disodium hydrogenphosphate, and sodium pyrophosphate dehydrate tended to enhance the whiteness. The table also shows that the use of potassium salt also had whitening effect. In the case of using 7.3 parts by weight of quillaja

| | Examples using gelatin | | | | | | | | | |
|---|---|---|---|---|---|---|---|---|---|---|
| Formulation | 10-1 | 10-2 | 10-3 | 10-4 | 10-5 | 10-6 | 10-7 | 10-8 | 10-9 | 10-10 |
| Gelatin | 100 | 100 | 100 | 100 | 100 | 100 | 100 | 100 | 100 | 100 |
| Na malale | 5 | | | 5 | | | | | | 15 |
| 2Na succinate | | 5 | | | 5 | | | | | |
| Na polyphosphate | | | 5 | | | 5 | | | | |
| Na bicarbonate | | | | | | | 5 | | | |
| K acetate | | | | | | | | | | |
| K carbonate | | | | | | | | | | |
| 2K hydrogenphosphate | | | | | | | | | | |
| K dihydrogenphosphate | | | | | | | | | | |
| 2Na hydrogenphosphate | | | | | | | | | | |
| Na dihydrogenphosphate | | | | | | | | | | |
| Na pyrophosphate dehydrate | | | | | | | | | | |
| Sucrose monolaurate ester | | | | 5 | 5 | 5 | 5 | | 5 | 15 |
| PEP101 | 5 | 5 | 5 | | | | | 5 | | |
| Qullaja saponin | | | | | | | | | | |
| Additive amount | 10 | 10 | 10 | 10 | 10 | 10 | 10 | 5 | 5 | 30 |
| White-color proportion | α | α | α | δ | δ | α | δ | α | δ | δ |
| White-color depth | γ | γ | α | δ | δ | a | δ | γ | δ | δ |
| Manufacturing method | C | C | C | C | C | C | C | C | C | C |

| | Examples using gelatin | | | | | | | | |
|---|---|---|---|---|---|---|---|---|---|
| Formulation | 10-11 | 10-12 | 10-13 | 10-14 | 10-15 | 10-16 | 10-17 | 10-18 | 10-19 |
| Gelatin | 100 | 100 | 100 | 100 | 100 | 100 | 100 | 100 | 100 |
| Na malale | | | | | | | | | |
| 2Na succinate | | | | | | | | | |
| Na polyphosphate | | | | | | | | 5 | |
| Na bicarbonate | | | | | | | | | |
| K acetate | 5 | | | | | | | | |
| K carbonate | | 5 | | | | | | | |
| 2K hydrogenphosphate | | | 5 | | | | | | |
| K dihydrogenphosphate | | | | 5 | | | | | |
| 2Na hydrogenphosphate | | | | | 5 | | | | |
| Na dihydrogenphosphate | | | | | | 5 | | | |
| Na pyrophosphate dehydrate | | | | | | | 5 | | 5 |
| Sucrose monolaurate ester | 5 | 5 | 5 | 5 | 5 | 5 | 5 | | |
| PEP101 | | | | | | | | | |
| Qullaja saponin | | | | | | | | 7.3 | 7.3 |
| Additive amount | 10 | 10 | 10 | 10 | 10 | 10 | 10 | 12.3 | 12.3 |
| White-color proportion | δ | α | α | δ | α | α | α | α | α |
| White-color depth | δ | δ | δ | δ | α | δ | α | α | α |
| Manufacturing method | C | C | C | C | C | C | C | C | C |

Table 10 shows the results of testing by use of gelatin as the film base material, together with polyoxyethylene (105) polyoxypropylene (5) glycol (PEP101), sucrose monolaurate ester or quillaja saponin as the surfactant. In the cases saponin, and either 5 parts by weight of sodium polyphosphate or 5 parts by weight of sodium pyrophosphate dehydrate rendered the film having both an excellent white-color proportion and an excellent white-color depth.

EXAMPLES

Some examples of the present invention will be provided below to describe specifically the present invention, but the examples below are not the only possible forms of the present invention.

Example 1: Case 1 of Using Hydroxypropyl Methylcellulose as Film Base Material A film forming aqueous solution was prepared by adding, into an about 20% hydroxypropyl methylcellulose solution, an aqueous solution containing 2.5 parts by weight (with the amount of the hydroxypropyl methylcellulose being 100 parts by weight) of sodium malate and 2.5 parts by weight of polyoxyethylene (105) polyoxypropylene (5) glycol. The resultant solution was poured onto a glass plate heated to about 105° C., and then the glass plate and the solution thereon were heated at 60° C. for 15 minutes. Thus formed was a white-colored film.

Example 2: Case 2 of Using Hydroxypropyl Methylcellulose as Film Base Material A film forming aqueous solution was prepared by adding, into an about 20% hydroxypropyl methylcellulose (a mixed HPMC of HPMC2906 and HPMC2910) solution, an aqueous solution containing 2.5 parts by weight (with the amount of the hydroxypropyl methylcellulose being 100 parts by weight) of dipotassium hydrogenphosphate and 2.5 parts by weight of sucrose monolaurate ester. The resultant solution was poured onto a glass plate heated to about 105° C., and then the glass plate and the solution thereon were heated at 60° C. for 15 minutes. Thus formed was a white-colored film.

Similar films were formed by replacing the salts added in the above-described method with disodium hydrogenphosphate, sodium dihydrogenphosphate, potassium carbonate, potassium dihydrogenphosphate, and sodium bicarbonate.

Each of these films got rating "a" for both the white-color proportion and the white-color depth.

Example 3: Case of Using Pullulan as Film Base Material

A film forming aqueous solution was prepared by adding, into an about 22% pullulan solution, an aqueous solution containing 2.5 parts by weight (with the amount of the pullulan being 100 parts by weight) of polyoxyethylene (105) polyoxypropylene (5) glycol. The resultant solution was poured onto a glass plate applied with a mold releasing agent and heated to about 60° C., and then was dried at room temperature. Thus formed was a white-colored film.

Example 4: Case of Using Gelatin as Film Base Material

A film forming aqueous solution was prepared by adding, into an about 34% gelatin solution, an aqueous solution containing 5 parts by weight (with the amount of the gelatin being 100 parts by weight) of sodium polyphosphate and 5 parts by weight of sucrose monolaurate ester. The resultant solution was poured onto a glass plate applied with a mold releasing agent and heated to about 80° C., and then was dried at room temperature. Thus formed was a white-colored film.

Example 5: Light-Blocking Property (Transmittance of Film)

The light-blocking effects were assessed for the white-colored films manufactured in accordance with the method of Example 1.

Each of the test samples was a piece of the film having a thickness of 100±10 μm, and the transmittance of each test sample was measured for a light with a wavelength within a range from 1100 nm to 190 nm by use of a spectrophotometer. The test results confirmed that the light transmittance was reduced by the formation of the white-colored film and that the white-colored film had a light-blocking effect.

Figure 1B:
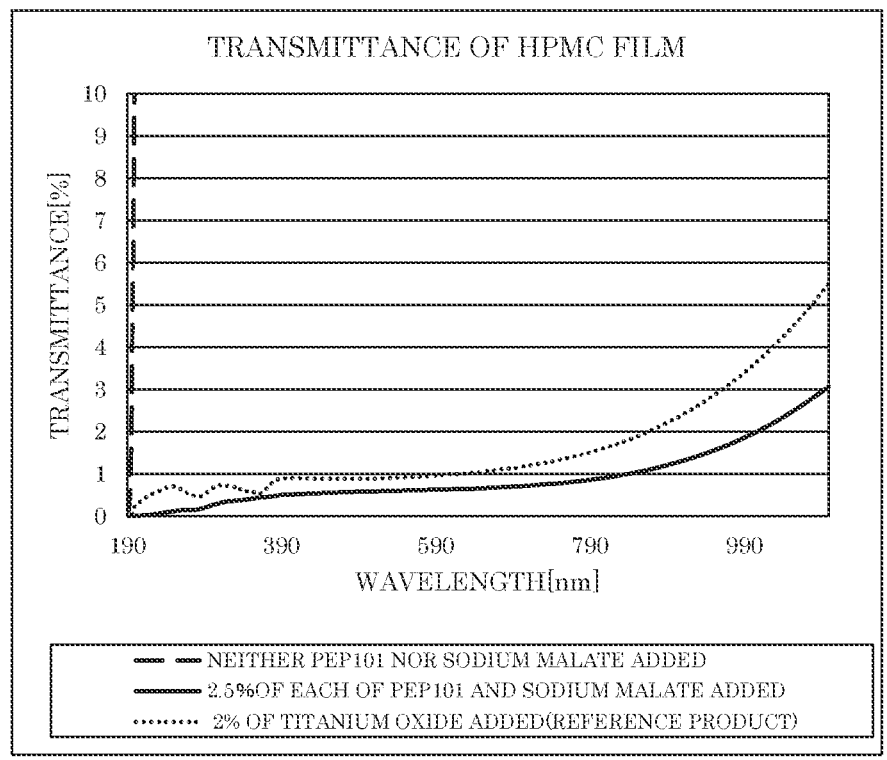
FIG. 1B shows the graph of FIG. 1A with a different Y-axis scale.

FIGS. 1A and 1B show: the measured transmittance of a white-colored film formed by adding, into an about 20% hydroxypropyl methylcellulose solution, an aqueous solution containing 2.5 parts by weight (the amount of the hydroxypropyl methylcellulose being 100 parts by weight) of sodium malate and 2.5 parts by weight of polyoxyethylene (105) polyoxypropylene (5) glycol, and then by pouring the resultant solution onto a glass plate heated to about 105° C. and thus heating the plate solution at 60° C. for 15 minutes; the measured transmittance of a film formed by pouring an about 20% hydroxypropyl methylcellulose solution onto a glass plate heated up to about 105° C. and heating the glass plate and the solution thereon at 60° C. for 15 minutes: and the measured transmittance of a film manufactured by the above-described manufacturing method except for the non-use of any whitening agent at all. A white-colored film serving as a general control product using titanium oxide as the light-blocking agent was formed: by adding, into an about 20% hydroxypropyl methylcellulose solution, a suspension containing 2 parts by weight of titanium oxide (the amount of the hydroxypropyl methylcellulose being 100 parts by weight), and then by pouring the resultant solution onto a glass plate heated to about 105° C. and heating the glass plate and the solution thereon at 80° C. for 15 minutes.

Figure 2A:
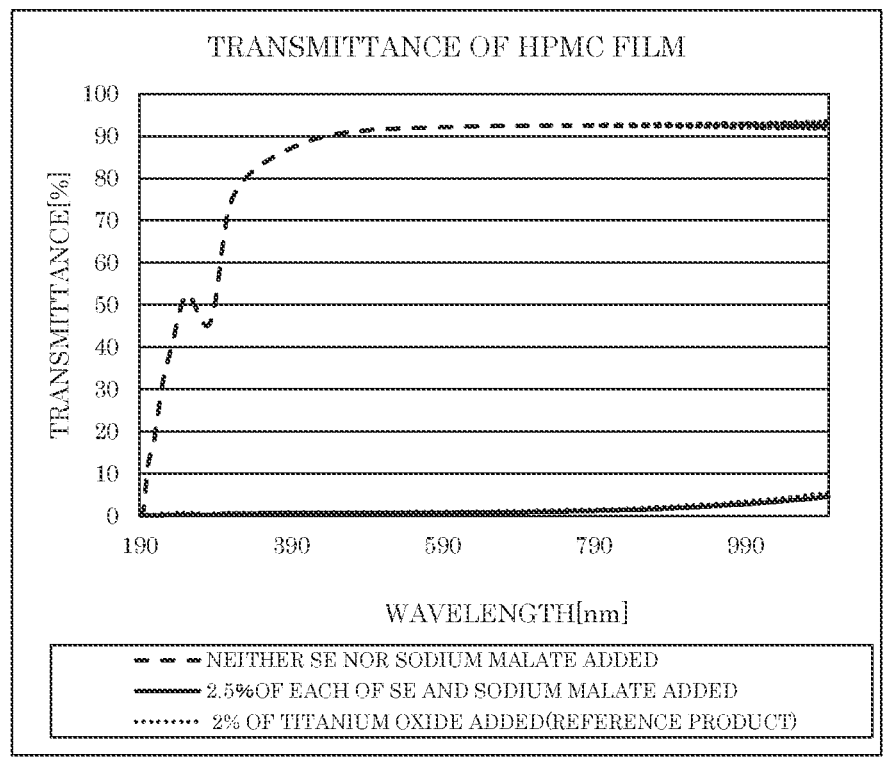
FIG. 2A shows: the light-blocking effect of a white-colored film manufactured by use of a whitening agent containing 2.5 parts by weight of sodium malate and 2.5 parts by weight of sucrose monolaurate ester along with 100 parts by weight of hydroxypropyl methylcellulose; and the light-blocking effect of a film manufactured without using the whitening agent.
Figure 2B:
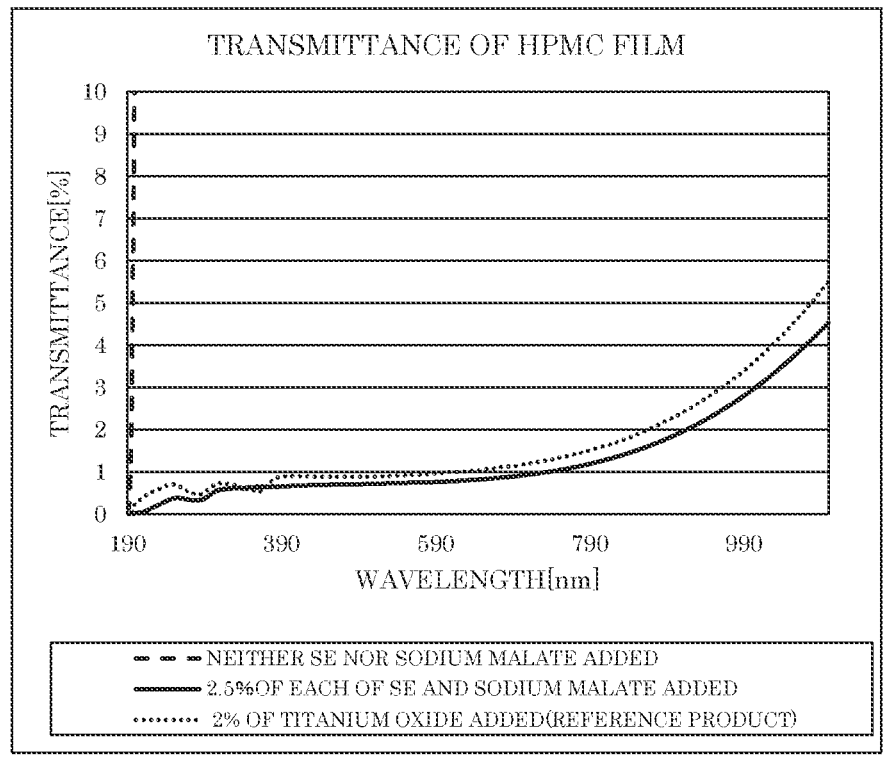
FIG. 2B shows the graph of FIG. 1A with a different Y-axis scale.

FIGS. 2A and 2B show: the measured transmittance of a white-colored film formed by adding, into an about 20% hydroxypropyl methylcellulose solution, an aqueous solution containing 2.5 parts by weight (the amount of the hydroxypropyl methylcellulose being 100 parts by weight) of sodium malate and 2.5 parts by weight of sucrose monolaurate ester, and then by pouring the resultant solution onto a glass plate heated to about 105° C. and heating the glass plate and the solution thereon at 60° C. for 15 minutes; and the measured transmittance of a film manufactured by the above-described manufacturing method except for the non-use of any whitening agent at all. A white-colored film serving as a general control product using titanium oxide as the light-blocking agent was formed: by adding, into an about 20% hydroxypropyl methylcellulose solution, a suspension containing 2 parts by weight of titanium oxide (the amount of the hydroxypropyl methylcellulose being 100 parts by weight), and then by pouring the resultant solution onto a glass plate heated to about 105° C. and heating the glass plate and the solution thereon at 60° C. for 15 minutes.

Example 6: Solubility of Film

A film forming aqueous solution was prepared by adding, into an about 20% hydroxypropyl methylcellulose solution, an aqueous solution containing 1.25 parts by weight (with the amount of the hydroxypropyl methylcellulose being 100 parts by weight) of sodium malate and 1.25 parts by weight of polyoxyethylene (105) polyoxypropylene (5) glycol. The resultant solution was poured onto a glass plate heated to about 105° C., and then the glass plate and the solution thereon were heated at 60° C. for 15 minutes. Thus formed was a white-colored film. The solubility of the white-colored film in water was assessed. Each of the test samples was a piece of the film having a thickness of 100±10 μm, and the testing method employed was the paddle method selected from the solubility test methods specified by the Japanese pharmacopoeia. The solubility of the hydroxypropyl methylcellulose was assessed under the following conditions.

Figure 3A:
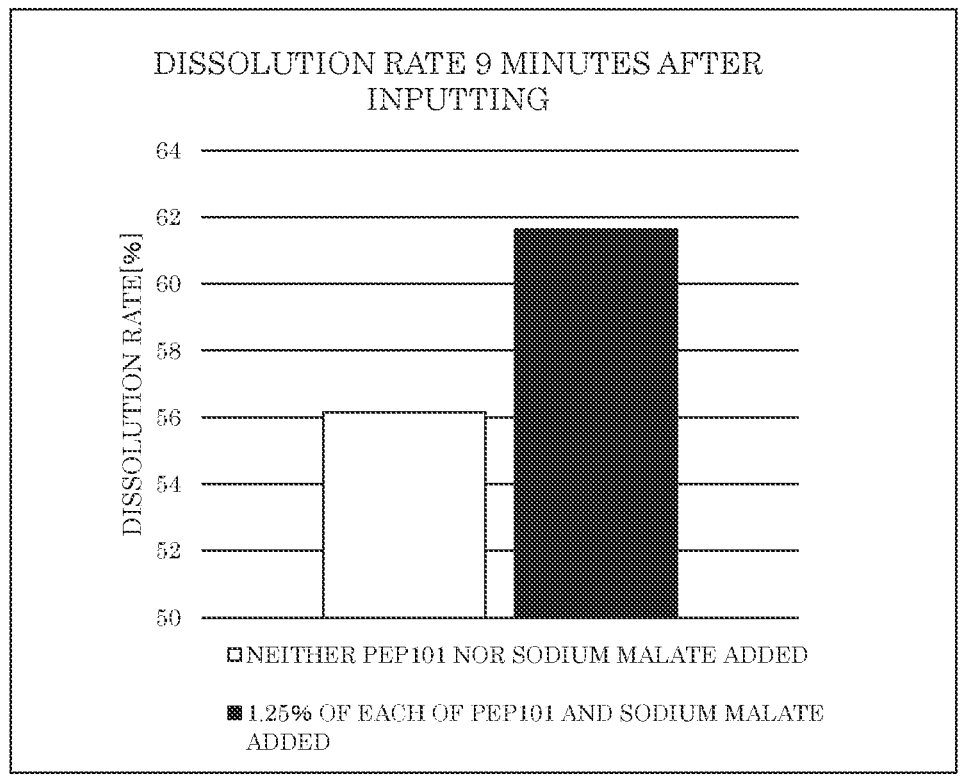
FIG. 3 shows dissolution rate of a white-colored film manufactured by use of a whitening agent containing 1.25 parts by weight of sodium malate and 1.25 parts by weight of polyoxyethylene (105) polyoxypropylene (5) glycol along with 100 parts by weight of hydroxypropyl methylcellulose; and the dissolution rate of a film not containing the whitening agent. The dissolution rates measured at the time of 9 minutes later and at the time of 15 minutes later are shown for each of the films.
Figure 3B:
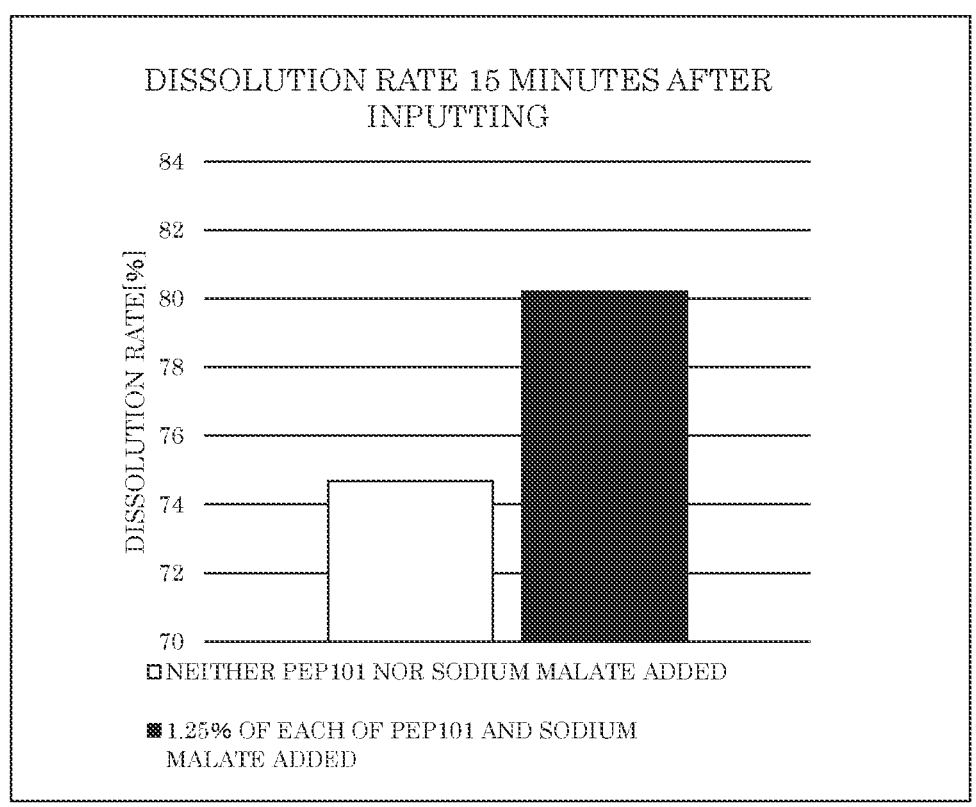

Test solution: Deionized water, Test solution amount: 400 mL,
Test solution temperature: 37±0.5° C.
Paddle revolutions: 50 rpm The test result confirmed that the dissolution rate was improved after the start of the solubility test (see FIGS. 3A and 3B)

Example 7: Colorability of Film

A film forming aqueous solution was prepared by adding, into an about 20% hydroxypropyl methylcellulose (a mixture of HPMC2910 and HPMC2208) solution, an aqueous solution containing 1.25 parts by weight (the amount of the hydroxypropyl methylcellulose being 100 parts by weight) of sodium malate, 5 parts by weight of sucrose monolaurate ester, and 1 part by weight of Yellow No. 5. The resultant solution was poured onto a glass plate heated to about 105° C. (note that the solution was poured onto the glass plate at the timing when the glass plate was cooled down to 70° C. (the temperature was measured by use of a radiation thermometer)), and then the glass plate and the solution thereon were heated at 60° C. for 15 minutes. Thus manufactured was a colored film. A film forming aqueous solution was prepared by adding, into an about 34% gelatin solution, an aqueous solution containing 5 parts by weight (the amount of the gelatin being 100 parts by weight) of the sodium polyphosphate, 5 parts by weight of sucrose monolaurate ester, and 1 part by weight of the gardenia red colorant. The resultant solution was poured onto a glass plate applied with a mold releasing agent and heated to about 60° C., and then was dried at room temperature. Thus manufactured was a colored film. A film forming aqueous solution was prepared by adding, Into an about 34% gelatin solution, an aqueous solution containing 5 parts by weight (the amount of the gelatin being 100 parts by weight) of the sodium polyphosphate, 5 parts by weight of sucrose monolaurate ester, and 1 part by weight of the gardenia blue colorant. The resultant solution was poured onto a glass plate applied with a mold releasing agent and heated to about 60° C., and then was dried at room temperature. Thus manufactured was a colored film. A film forming aqueous solution was prepared by adding, into an about 34% gelatin solution, an aqueous solution containing 5 parts by weight (the amount of the gelatin being 100 parts by weight) of the sodium polyphosphate, 5 parts by weight of sucrose monolaurate ester, and 1 part by weight of a green colorant (a mixed colorant of the gardenia blue colorant and the safflower colorant). The resultant solution was poured onto a glass plate applied with a mold releasing agent and heated to about 60° C., and then was dried at room temperature. Thus manufactured was a colored film.

In addition, a film forming aqueous solution was prepared by adding, into an about 22% pullulan solution, an aqueous solution containing 2.5 parts by weight (with the amount of the pullulan being 100 parts by weight) of polyoxyethylene (105) polyoxypropylene (5) glycol and 1 part by weight of the gardenia red colorant. The resultant solution was poured onto a glass plate applied with a mold releasing agent and heated to about 60° C., and then was dried at room temperature. Thus manufactured was a colored film. AN the test results confirmed that an opaque colored film was manufactured in every above-described case.

INDUSTRIAL APPLICABILITY

A film forming composition of the present invention containing a polymer dissolved in water and a whitening agent including either a surfactant alone or a combination of a surfactant and a salt allows the resultant film to be whitened and opacified by the surfactant without using titanium oxide, whose carcinogenicity has already been reported. Light-blocking property can thus be given to the film of the present invention. The film forming composition has an excellent solubility. The white color of the film cannot be removed even when the film is rubbed. A white-color film thus formed is stable for a prolonged period of time. When used together with a colorant, the film forming composition of the present invention can provide an opaque colored film. Hence, the film of the present invention is very useful especially as a material for capsules to contain contents such as drugs for humans and animals, agricultural chemicals, cosmetics, and health food products. The film is also very useful as a coating material for tablets and granules, as an edible film, and as an ink for food products.

The invention claimed is:
1. A single layer white film, comprising:
a single film-forming polymer as a base material of the single layer white film, wherein the single film-forming polymer is either gelatin or pullulan; and
a whitening agent that includes either a surfactant or both a surfactant and a water-soluble salt,
wherein the surfactant is a fatty acid ester of polyhydric alcohol, polyethylene glycol, polypropylene glycol, polyalkylene oxide derivative, alkyl sulfate ester salt, and/or a saponin; and
wherein the single layer white film is free from a white-color pigment.
2. The single layer white film according to claim 1,
wherein the fatty acid ester of polyhydric alcohol is a sucrose fatty acid ester, sorbitan fatty acid ester, glycerin fatty acid ester, or polyoxysorbitan fatty acid ester;
the polyalkylene oxide derivative is a polyoxyethylene polyoxypropylene glycol, polyoxyethylene alkyl ether, or polyoxyethylene fatty acid ester; and
the saponin is either a triterpenoid saponin or steroid saponin.
3. The single layer white film according to claim 1,
wherein the surfactant is polyoxyethylene polyoxypropylene glycol, sucrose monolaurate ester, sucrose palmitate ester, sorbitan monolaurate ester, Polysorbate 80, sodium lauryl sulfate, quillaja saponin, ginseng saponin, soybean saponin, sophora saponin, tea seed saponin, beet saponin, yucca saponin, or glycyrrhizin.
4. The single layer white film according to claim 1,
wherein whiteness of the single layer white film is adjusted by a total amount of the surfactant within a range from 0.5 parts by weight to 30 parts by weight while an amount, in dry weight, of the film-forming polymer is defined as 100 parts by weight.
5. The single layer white film according to claim 1,
wherein whiteness of the single layer white film is adjusted by a total amount of the surfactant within a range from 0.7 parts by weight to 30 parts by weight while an amount, in dry weight, of the film-forming polymer is defined as 100 parts by weight.

6. The single layer white film according to claim 1, wherein whiteness of the single layer white film is adjusted by a total amount of the surfactant within a range from 1.0 part by weight to 30 parts by weight while an amount, in dry weight, of the film-forming polymer is defined as 100 parts by weight.

7. The single layer white film according to claim 1, wherein whiteness of the single layer white film is adjusted by a total amount of the surfactant within a range from 0.5 parts by weight to 15 parts by weight while an amount, in dry weight, of the film-forming polymer is defined as 100 parts by weight.

8. The single layer white film according to claim 1, wherein the water-soluble salt to be added is a sodium salt and/or a potassium salt and/or an ammonium salt.

9. The single layer white film according to claim 1, wherein the water-soluble salt to be added to the film-forming polymer is one or more salts selected from sodium malate, sodium succinate, sodium citrate, sodium polyphosphate, sodium bicarbonate, dipotassium hydrogenphosphate, disodium hydrogenphosphate, sodium dihydrogenphosphate, potassium carbonate, potassium dihydrogenphosphate, and sodium pyrophosphate dehydrate,
the whiteness of the single layer white film is changed by the total amount of the water-soluble salt within a range from 0.5 parts by weight to 30 parts by weight, while an amount, in dry weight, of the film-forming polymer is defined as 100 parts by weight.

10. The single layer white film according to claim 1, further comprising a dye or a pigment to provide the single layer white film with a color other than white.

11. A capsule that is made of the single layer white film according to claim 1 and that is suitable for oral delivery.

12. The capsule according to claim 11, wherein the capsule is filled with a drug, a cosmetic or a health food product.

13. The capsule according to claim 11, wherein a combination of the film-forming polymer and the surfactant is a combination of:
gelatin and sucrose monolaurate ester;
gelatin and polyoxyethylene polyoxypropylene glycol;
gelatin and the saponin; or
pullulan and polyoxyethylene polyoxypropylene glycol.

14. A film forming composition for forming the single layer white film according to claim 1, the film forming composition comprising:
the single film-forming polymer dissolved in water, and the whitening agent.

15. A method of manufacturing a single layer white film or a capsule suitable for oral delivery, the single layer white film and the capsule being white and free from a white-color pigment, the method comprising:
providing gelatin or pullulan as a film-forming polymer to provide a base material of the single layer white film or capsule; and
providing, as a whitening agent, either a surfactant or both a surfactant and a water-soluble salt;
combining the film-forming polymer and the whitening agent to provide a film-forming composition; and
forming the single layer white film or the capsule from the film-forming composition;
wherein the surfactant is a fatty acid ester of polyhydric alcohol, polyethylene glycol, polypropylene glycol, polyalkylene oxide derivative, an alkyl sulfate ester salt, or a saponin.

16. The capsule according to claim 13, wherein the saponin is quillaja saponin, ginseng saponin, soybean saponin, sophora saponin, tea seed saponin, beet saponin, yucca saponin, or glycyrrhizin.

17. A white film comprising:
a film-forming polymer that is a cellulose derivative; and
a whitening agent that includes either a surfactant or both a surfactant and a water-soluble salt, wherein the surfactant is an alkyl sulfate ester salt and/or a saponin; and
wherein the white film is free from a white-color pigment.

18. The film according to claim 17, wherein the cellulose derivative is hydroxypropyl methylcellulose (HPMC).

19. The film according to claim 17, wherein the surfactant is sodium lauryl sulfate, quillaja saponin, ginseng saponin, soybean saponin, sophora saponin, tea seed saponin, beet saponin, yucca saponin, or glycyrrhizin.

20. The film according to claim 17, wherein whiteness of the film is adjusted by a total amount of the surfactant within a range from 0.5 parts by weight to 30 parts by weight while an amount, in dry weight, of the film-forming polymer is defined as 100 parts by weight.

21. The film according to claim 17, wherein whiteness of the film is adjusted by a total amount of the surfactant within a range from 0.7 parts by weight to 30 parts by weight while an amount, in dry weight, of the film-forming polymer is defined as 100 parts by weight.

22. The film according to claim 17, wherein whiteness of the film is adjusted by a total amount of the surfactant within a range from 1.0 part by weight to 30 parts by weight while an amount, in dry weight, of the film-forming polymer is defined as 100 parts by weight.

23. The film according to claim 17, wherein whiteness of the film is adjusted by a total amount of the surfactant within a range from 0.5 parts by weight to 15 parts by weight while an amount, in dry weight, of the film-forming polymer is defined as 100 parts by weight.

24. The film according to claim 17, wherein the water-soluble salt to be added is a sodium salt and/or a potassium salt and/or an ammonium salt.

25. The film according to claim 17, wherein the water-soluble salt to be added to the film-forming polymer is one or more salts selected from sodium malate, sodium succinate, sodium citrate, sodium polyphosphate, sodium bicarbonate, dipotassium hydrogenphosphate, disodium hydrogenphosphate, sodium dihydrogenphosphate, potassium carbonate, potassium dihydrogenphosphate, and sodium pyrophosphate dehydrate, and wherein the whiteness of the film is changed by the total amount of the water-soluble salt within a range from 0.5 parts by weight to 30 parts by weight, while an amount, in dry weight, of the film-forming polymer is defined as 100 parts by weight.

26. The film according to claim 17, further comprising a dye or pigment to provide the film with a color other than white.

27. A capsule that is made of the film according to claim 17 and that is suitable for oral delivery.

28. The capsule according to claim 27, wherein the cellulose derivative is hydroxypropyl methylcellulose (HPMC).

29. The capsule according to claim 28, wherein the capsule is filled with a drug, a cosmetic or a health food product.

30. The capsule according to claim 27, wherein a combination of the film-forming polymer and the surfactant is a combination of (i) hydroxypropyl methylcellulose (HPMC) and (ii) a saponin selected from quillaja saponin, ginseng saponin, soybean saponin, sophora saponin, tea seed saponin, beet saponin, yucca saponin, or glycyrrhizin.

31. A method of manufacturing a film or a capsule suitable for oral delivery, the film and the capsule being white and free from a white-color pigment, the method comprising:
- providing a cellulose derivative as a film-forming polymer; and
- providing, as a whitening agent, either (i) an alkyl sulfate ester salt or a saponin; or (ii) a combination of (a) an alkyl sulfate ester salt and a water-soluble salt, or (b) a saponin and a water-soluble salt;
- combining the film-forming polymer and the whitening agent to provide a film-forming composition; and
- forming the film or the capsule from the film-forming composition.

\* \* \* \* \*